United States Patent [19]

Miller et al.

[11] 4,414,400
[45] Nov. 8, 1983

[54] PROCESS FOR THE PRODUCTION OF TETRONIC ACID

[75] Inventors: Raimund Miller, Hackensack, N.J.; Leander Tenud, Visp, Switzerland

[73] Assignee: Lonza Ltd., Gampel, Switzerland

[21] Appl. No.: 388,432

[22] Filed: Jun. 14, 1982

[30] Foreign Application Priority Data

Jun. 17, 1981 [CH] Switzerland .......................... 3982/81

[51] Int. Cl.³ ............................................ C07D 307/60
[52] U.S. Cl. ...................................... 549/313; 560/174
[58] Field of Search .......................................... 549/313

[56] References Cited

U.S. PATENT DOCUMENTS

Re. 28,242  11/1974  Boosen ................................. 549/313
3,824,255   7/1974   Boosen ................................. 549/313

FOREIGN PATENT DOCUMENTS 18162    10/1980  European Pat. Off. .
2143709  3/1972   Fed. Rep. of Germany .
503722   2/1971   Switzerland .
529128   10/1972  Switzerland .

OTHER PUBLICATIONS

Baan et al., "The Total Synthesis of the Antibiotic Malonomicin," Tetrahedron, vol. 34, (1978), pp. 223 to 231.

Primary Examiner—Norma S. Milestone
Attorney, Agent, or Firm—Fisher, Christen & Sabol

[57] ABSTRACT

Process for the production of tetronic acid from 4-haloacetoacetic ester. The 4-haloacetoacetic ester is transformed into the corresponding 4-tertiary-butoxyacetoacetic ester and the latter is converted by cyclizing ether cleavage into tetronic acid. Preferably the cyclizing ether cleavage is carried out thermolytically at a temperature above 100° C. or is carried out by treatment with an acid at a temperature of 0° to 30° C. Tertiary-butoxyacetoacetic acid ethyl ester is a new compound.

13 Claims, No Drawings

PROCESS FOR THE PRODUCTION OF TETRONIC ACID

BACKGROUND OF THE INVENTION

1. Field of the Invention

The invention relates to a process for the production of tetronic acid from 4-haloacetoacetic ester.

2. Prior Art

Tetronic acid, which is used among other things as an accelerator for photographic development, is known to be produced from 4-mono-haloacetoacetic ester or acid. According to the Swiss Pat. No. 503,722, 4-chloroacetoacetic ester is reacted with an aromatic amine to produce 3-arylaminocrotolactone, and the tetronic acid is liberated from such lactone by means of a mineral acid. The disadvantage of such method is that the isolation of the tetronic acid can only be realized by means of high vacuum sublimation. According to Swiss Pat. No. 529,128, 4-haloacetoacetic acid is reacted with alkali in aqueous solution. By treatment with a mineral acid the tetronic acid is liberated. Here too the isolation of the tetronic acid must be accomplished by means of high vacuum sublimation; moreover, the achieved yield is only 43 to 44 percent.

BROAD DESCRIPTION OF THE INVENTION

An object of the invention is to provide a process for the production of tetronic acid. Another object of the invention is to provide a process for the production of tetronic acid which avoids the above-stated disadvantages of the prior art processes. A further advantage of the invention is to provide certain new compounds and compositions. Other objects and advantages of this invention are set out herein or are obvious to one ordinarily skilled in the art.

The objects and advantages of this invention are achieved by the process and compound of this invention.

The invention includes the process of preparing tetronic acid from 4-haloacetoacetic ester. The 4-haloacetoacetic ester is converted or transformed into the corresponding 4-tertiary butoxyacetoacetic ester. The latter ester is converted by cyclizing ether cleavage into the tetronic acid. Preferably the cyclizing ether cleavage is carried out thermolytically at a temperature above 100° C. or is carried out by treatment with acids at a temperature from 0° to 30° C.

The invention includes 4-tertiary-butoxyacetoacetic acid alkyl esters, such as, 4-tertiary-butoxyacetoacetic acid ethyl ester.

The invention also includes a composition composed of an acid, water and a 4-tertiary-butoxyacetoacetic alkyl ester. The invention further includes a composition composed of an alkali salt of tertiary butyl alcohol, an organic solvent and a 4-haloacetoacetic alkyl ester.

DETAILED DESCRIPTION OF THIS INVENTION

As used herein, all parts, ratios, percentages and proportions are on a weight basis, unless otherwise stated herein or otherwise obvious herefrom to one ordinarily skilled in the art.

The transfer of the 4-haloacetoacetic ester into the tertiary-butoxyacetoacetic ester is accomplished effectively by allowing an alkali salt, preferably the sodium salt, of the tertiary butyl alcohol to act on the 4-haloacetoacetic ester in an organic solvent. Other useful alkali salts include the potassium and lithium salts of tertiary butyl alcohol. All suitable compounds (e.g., other aprotic organic solvents) can be used as solvents, advantageously however the solvent is dimethyl sulfoxide or tetrahydrofuran. The reaction temperature should be kept effectively at 0° to 50° C.

In a preferred embodiment, sodium hydride is suspended in tetrahydrofuran and tertiary butyl alcohol is added in doses. The γ-halogen acetoacetic ester, dissolved in tetrahydrofuran, is added in doses into the solution obtained in such way. The most effective reaction temperature is between 0° and 50° C.

After the reaction is completed, the tetrahydrofuran can be recaptured for distillation. The tertiary butoxyacetoacetic acid ethyl ester produced according to this method of operation is a viscous yellowish oil having a $Kp_{0.3}$ of 61° to 65° C.

The cyclizing ether cleavage can be carried out (i) by temperature treatment of the tertiary-butoxyacetoacetic ester at a temperature above 100° C., preferably at a temperature of 150° to 280° C., or (ii) by treatment of the tertiary-butoxyacetoacetic ester by means of an acid, such as, hydrochloric acid, trifluoroacetic acid or an acid cation exchanger.

Whenever the cyclizing ether separation is carried out by means of temperature treatment, then such can be accomplished in a tube reactor with or without filling body or in a thin layer reactor. The tertiary-butoxyacetoacetic ester can be put on in liquid as well as in steam form.

As 4-haloacetoacetic ester, the 4-bromo- and 4-chloro-derivatives are normally used, especially the 4-chloro-derivatives. As esters, effectively those obtained from alcohols with 1 to 6 carbon atoms, such as, methyl alcohol, ethyl alcohol, propyl alcohol and butyl alcohol, are used. Preferably 4-chloroacetoacetic acid ethyl ester is used as the starting product.

Tetronic acid is 2,4-dioxo-tetrahydrofuan or β-ketobutyrolactone. Tetronic acid is useful as an accelerator for photographic development.

By way of summary, tetronic acid can be produced starting out from 4-haloacetoacetic ester by way of the 4-tertiary-butoxyacetoacetic ester or the like.

EXAMPLE 1

21.3 g of 80 percent sodium hydride was freed of white oil by washing three times with 30 ml of petroleum ether (boiling point: 40° to 60° C.) and was added to 300 ml of tetrahydrofuran. Then, while stirring, 25.57 g of tertiary butyl alcohol was added in doses in such a way that a reaction temperature of 40° C. was maintained. After hydrogen development was completed, a solution of 49.38 g (95.5 percent) of 4-chloroacetoacetic ethyl ester in 120 ml of tetrahydrofuran was added drop by drop during a 25 minute period. After 20 hours of stirring at ambient temperature, 250 ml of tetrahydrofuran was evaporated off on a vacuum rotation evaporator and the still-flowable residue was poured in a thin jet into a mixture of 45 g of concentrated HCl in 250 g of ice water. At the end of the addition, the pH adjusted itself to 5. Then such was extracted four times with ether. After washing and drying, the ether was evaporated on the vacuum rotation evaporator. The residue was distilled. 47.09 g (75.5 percent) of 4-tertiary-butoxyacetoacetic acid ethyl ester resulted.

5 g of the 4-tertiary-butoxyacetoacetic acid ethyl ester was dissolved in 10 ml of 18 percent HCl. The mixture was stirred at ambient temperature for 6 hours. Subsequently the HCl was drawn off in the vacuum rotation evaporator at a temperature below 30° C. The crystalline residue was dissolved in a little water and the water was drawn off in the vacuum rotation evaporator at a temperature below 30° C. This operation was once more repeated. 2.48 g of tetronic acid having a purity of 99.1 percent resulted, which corresponded to a yield of 100 percent related to the 4-tertiary-butoxyacetoacetic ester. The total yield, related to the 4-chloroester, amounted to 75.5 percent.

The 4-tertiary-butoxyacetoacetic ethyl ester is new and has the following characteristics:
IR (thin film)
  Bands: 2990 (vs), 1750 (vs), 1730 (vs), 1660 (m), 1370 (m), 1325 (m), and 1105 (m) cm$^{-1}$.

| NMR (10 percent in CCl$_4$) | | |
|---|---|---|
| $\delta$ = | 1.2 (S) | } 12 H |
| $\delta$ = | 1.29 (t) | |
| $\delta$ = | 4.20 (q, 2H) | ppm |
| $\delta$ = | 3.45 (S, 2H) | |
| $\delta$ = | 3.93 (S, 2H) | |

EXAMPLE 2

Using the procedure of Example 1, 4-chloroacetoacetic acid isopropyl ester was reacted with sodium tertiary butylate to produce 4-tertiary-butoxyacetoacetic acid isopropyl ester. The latter was converted using the procedure of Example 1 into tetronic acid by treatment with 18 percent hydrochloric acid. The yield was 77 percent.

EXAMPLE 3

Using the procedure of Example 1, 4-chloroacetoacetic acid-n-butyl ester was reacted with sodium tertiary butylate to produce 4-tertiary butoxyacetoacetic acid-n-butyl ester. Using the procedure of Example 1, the latter was converted into tetronic acid by treatment with 18 percent hydrochloric acid. The yield was 75.5 percent.

What is claimed is:

1. Process for the production of tetronic acid converting a 4-haloacetoacetic alkyl ester into the corresponding 4-tertiary-butoxyacetoacetic alkyl ester and converting the latter ester by cyclizing ether cleavage into tetronic acid.

2. Process as claimed in claim 1 wherein the alkyl moiety of the 4-haloacetoacetic alkyl ester has 1 to 4 carbon atoms.

3. Process as claimed in claim 2 wherein the 4-haloacetoacetic alkyl ester is 4-haloacetoacetic ethyl ester.

4. Process as claimed in claim 2 wherein the 4-haloacetoacetic alkyl ester is 4-chloroacetoacetic ethyl ester.

5. Process as claimed in claim 1 wherein the conversion is conducted by means of an alkali salt of tertiary butyl alcohol in the presence of an organic solvent.

6. Process as claimed in claim 5 wherein the alkali salt of tertiary butyl alcohol is the sodium salt of tertiary butyl alcohol.

7. Process as claimed in claim 5 wherein the organic solvent is dimethyl sulfoxide or tetrahydrofuran.

8. Process as claimed in claim 5 wherein the conversion is conducted at a temperature of 0° to 50° C.

9. Process as claimed in claim 1 wherein the cyclizing ether cleavage is carried out thermolytically at a temperature above 100° C.

10. Process as claimed in claim 9 wherein a temperature of 150° to 280° C. is used.

11. Process as claimed in claim 1 wherein the cyclizing ether cleavage is carried out by treatment with an acid at a temperature of 0° to 30° C.

12. Process as claimed in claim 7 wherein the acid is a mineral acid.

13. Process as claimed in claim 7 wherein the acid is hydrochloric acid, trifluoroacetic acid or an acid cation exchanger.

* * * * *